（12） United States Patent
Tanaka et al.

(10) Patent No.: US 10,165,930 B2
(45) Date of Patent: Jan. 1, 2019

(54) ENDOSCOPE

(71) Applicant: FUJIFILM Corporation, Tokyo (JP)

(72) Inventors: Toshizumi Tanaka, Kanagawa (JP);
Tomohiro Ohki, Kanagawa (JP);
Teruyuki Emura, Kanagawa (JP);
Sunao Hachisuka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 28 days.

(21) Appl. No.: 15/073,657

(22) Filed: Mar. 18, 2016

(65) Prior Publication Data

US 2016/0270634 A1     Sep. 22, 2016

(30) Foreign Application Priority Data

Mar. 20, 2015   (JP) ................. 2015-058345

(51) Int. Cl.
*A61B 1/00*     (2006.01)

(52) U.S. Cl.
CPC ...... *A61B 1/00098* (2013.01); *A61B 1/00137* (2013.01); *A61B 1/00142* (2013.01)

(58) Field of Classification Search
CPC ........................ A61B 1/00098; A61B 1/00101
USPC ................................. 600/106, 107, 127, 133
See application file for complete search history.

(56) References Cited

U.S. PATENT DOCUMENTS

| | | | | |
|---|---|---|---|---|
| 3,404,545 A | * | 10/1968 | Walker ...................... | F16D 3/04 |
| | | | | 464/104 |
| 5,562,600 A | * | 10/1996 | Matsuno ................ | A61B 1/018 |
| | | | | 600/107 |
| 2001/0044570 A1 | * | 11/2001 | Ouchi ................ | A61B 1/00098 |
| | | | | 600/107 |
| 2004/0082836 A1 | | 4/2004 | Hino | |
| 2007/0270638 A1 | * | 11/2007 | Kitano ............... | A61B 1/00098 |
| | | | | 600/104 |

FOREIGN PATENT DOCUMENTS

| | | |
|---|---|---|
| JP | H114804 | 1/1999 |
| JP | 2004-141315 | 5/2004 |
| JP | 2010-201020 | 9/2010 |
| JP | 2014-046167 | 3/2014 |

OTHER PUBLICATIONS

"Office Action of Japan Counterpart Application", dated Sep. 10, 2018, with English translation thereof, p. 1-p. 4.

* cited by examiner

*Primary Examiner* — Alexandra L Newton
*Assistant Examiner* — Rynae Boler
(74) *Attorney, Agent, or Firm* — JCIPRNET

(57) ABSTRACT

The endoscope includes: a rotating shaft in a distal end portion body of an insertion portion; an elevator which is coupled with one end of the rotating shaft; an elevator erecting lever which is coupled with the other end; an operating wire which rotates the rotating shaft through the elevator erecting lever to erect the elevator; a partition wall including a holding hole to support the rotating shaft; and a seal member disposed between the holding hole and the rotating shaft. The configuration of the rotating shaft and a positional relation between the rotating shaft and the seal member are improved so as to reduce time and labor taken for cleaning processing of the endoscope.

7 Claims, 13 Drawing Sheets

ENDOSCOPE

CROSS-REFERENCE TO RELATED APPLICATIONS

The present application claims priority under 35 U.S.C. § 119 to Japanese Patent Application No. 2015-058345, filed on Mar. 20, 2015. Each of the above application(s) is hereby expressly incorporated by reference, in their entirety, into the present application.

BACKGROUND OF THE INVENTION

Field of the Invention

The present invention relates to an endoscope including an elevator that controls the derivation direction of a treatment tool, in a distal end portion of an insertion portion.

Description of the Related Art

In an endoscope, various treatment tools are inserted in a treatment tool entry port provided in an operation portion, are led out from a treatment tool exit port opened in a distal end portion and are used for treatment. For example, various treatment tools are used such as a guide wire or a contrast tube in a duodenoscope, and a puncture needle in an ultrasonic endoscope, and, additionally, a forceps and a snare in a direct-view endoscope or a side-view endoscope. In such treatment tools, it is necessary to change the derivation direction in a distal end portion to treat a desired position in a subject, and, therefore, a treatment tool elevating mechanism (forceps elevator, hereinafter referred to as "elevator") is provided in the distal end portion.

As such a treatment tool elevating mechanism, there is known a mechanism in which an operating wire is attached to an elevator and extended to the proximal end side of an endoscope, and the elevator is rotated around a rotating shaft by performing push-pull operation on the operating wire with an operating lever provided in an operation portion so as to change the position of the elevator between a erecting position and a reclining position. Moreover, there is known a so-called lever-type mechanism in which an elevator erecting lever which is housed with an elevator across a partition wall is coupled to the elevator with a rotating shaft, an operating wire is attached to the elevator erecting lever, and the elevator is rotated around the rotating shaft by pushing and pulling the operating wire with an operating lever included in an operation portion so as to change the position of the elevator between a erecting position and a reclining position (see Japanese Patent Application Laid-Open No. 2014-046167, Japanese Patent Application Laid-Open No. 2010-201020, and Japanese Patent Application Laid-Open No. 2004-141315).

In such the treatment tool elevating mechanism, a seal member is disposed between the outer wall surface of a rotating shaft and the inner wall surface of a holding hole of a partition wall which rotatably supports this rotating shaft in order to form an airtight surface with this seal member. Thereby, blood and water, and so on, are prevented from entering from the elevator housing chamber side which houses the elevator to the erecting lever housing chamber side which houses the elevator erecting lever.

SUMMARY OF THE INVENTION

By the way, in an endoscope, it is necessary to perform cleaning processing using a cleaning solution or an antiseptic solution every time when it is used for various inspections or treatments. At this time, since a body of the distal end portion (distal end portion body) including a treatment tool elevating mechanism is miniaturized and its shape is complicated, the improvement of cleaning performance and the easiness of cleaning work, which are associated with the flow of the cleaning solution or the antiseptic solution, the insertion performance of a cleaning brush and the draining performance and so on, are requested. Especially, a coupling portion between the elevator and the rotating shaft requires cleaning processing since it is located on the elevator side with respect to the airtight surface formed by the seal member disposed between an inner wall surface of a holding hole and an outer wall surface of the rotating shaft. However, there is a problem that a gap of this coupling portion is small and it takes time and labor for the cleaning processing.

The present invention has been made considering such circumstances, and aims to provide an endoscope which can reduce the time and labor taken for the cleaning processing.

To achieve the object of the present invention, an endoscope includes: an insertion portion which includes a distal end and a proximal end; an operation portion which is provided on a proximal end side of the insertion portion and includes an operating member; a distal end portion body which is provided on a distal end side of the insertion portion; a rotating shaft which is rotatably supported in the distal end portion body; an elevator which is coupled with one end of the rotating shaft; an elevator erecting lever which is coupled with the other end of the rotating shaft; an operating wire which includes a proximal-end-side coupling portion coupled with the operating member and a distal-end-side coupling portion coupled with the elevator erecting lever, the operating wire configured to rotate the rotating shaft through the elevator erecting lever by operation of the operating member to erect the elevator; a partition wall which includes a holding hole to support the rotating shaft, is a part of the distal end portion body and is provided between the elevator and the elevator erecting lever; and a seal member which is disposed between the holding hole and the rotating shaft, wherein: the rotating shaft includes a first rotating shaft and a second rotating shaft; the first rotating shaft has one end connected with the elevator erecting lever and another end provided with a first coupling portion; the second rotating shaft has one end connected with the elevator and another end provided with a second coupling portion which is coupled with the first coupling portion in a relativity unrotatable manner; and a coupling position in which the first coupling portion and the second coupling portion are coupled with each other is disposed on a side of the elevator erecting lever with respect to the seal member.

According to the present invention, since the coupling position between the first coupling portion of the first rotating shaft and the second coupling portion of the second rotating shaft is located on the elevator erecting lever side with respect to the seal member, a liquid does not enter to reach this coupling position, and the cleaning processing of the coupling portion between the first rotating shaft and the second rotating shaft becomes unnecessary.

In an endoscope according to another aspect of the present invention, any one of the first coupling portion and the second coupling portion has a convex portion that projects in an axis direction of the rotating shaft, another one of the first coupling portion and the second coupling portion includes a concave portion that is concave in the axis direction of the rotating shaft, and the first rotating shaft and the second rotating shaft are coupled in a relatively unrotatable manner by fitting the convex portion and the concave portion to each other. Thus, it is possible to integrally swing the elevator and the erecting lever through the rotating shaft.

In an endoscope according to another aspect of the present invention, a positioning portion configured to position the seal member in an axis direction of the rotating shaft is included, and the positioning portion includes a first engagement portion provided in the second rotating shaft and a second engagement portion provided in the seal member, and positions the seal member in the axis direction by engaging the first engagement portion and the second engagement portion with each other. By this means, the seal member is prevented from moving toward the erecting lever side beyond (over) the coupling position by the rotation of the rotating shaft and the slide contact with the inner wall surface of the holding hole.

In an endoscope according to another aspect of the present invention, a positioning portion configured to position the seal member in an axis direction of the rotating shaft is included, and the positioning portion includes a first engagement portion provided in an inner wall surface of the holding hole of the partition wall and a second engagement portion provided in the seal member, and positions the seal member in the axis direction by engaging the first engagement portion and the second engagement portion with each other. By this means, the seal member is prevented from moving toward the erecting lever side beyond (over) the coupling position by the rotation of the rotating shaft and the slide contact with the inner wall surface of the holding hole.

An endoscope of the present invention can reduce time and labor taken for cleaning processing.

DETAILED DESCRIPTION OF THE EMBODIMENTS

Figure 1:
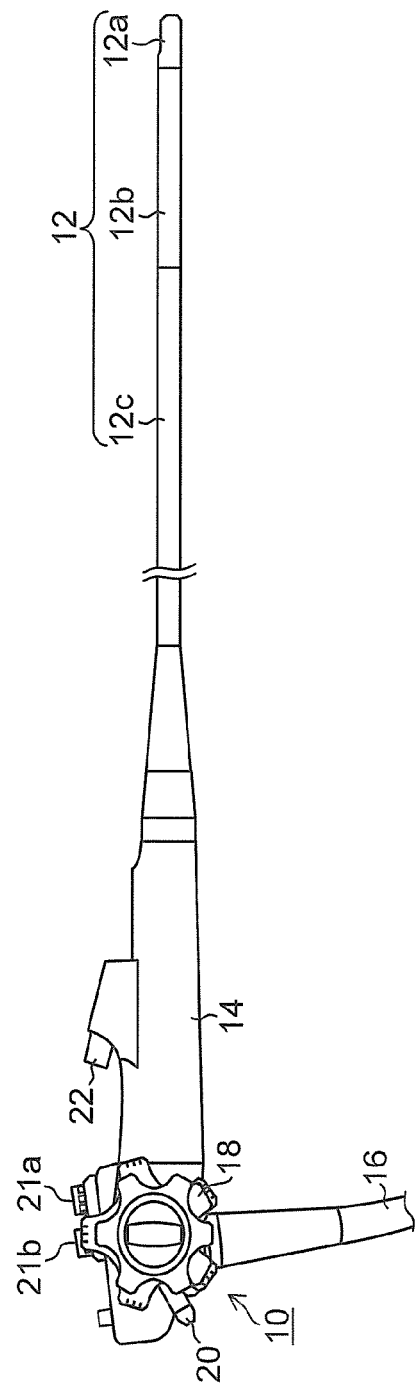
FIG. 1 is a side view illustrating an overall configuration of an endoscope.

An endoscope according to the present invention is described with reference to the accompanying drawings below. FIG. 1 is a side view illustrating an overall configuration of an endoscope 10.

<Overall Configuration of Endoscope>

As illustrated in FIG. 1, the endoscope 10 includes an insertion portion 12 to be inserted in the body of a subject, and an operation portion 14 is coupled with the proximal end side of the insertion portion 12. A universal cord 16 is connected with the operation portion 14, and the endoscope 10 is connected with a light source device, an image processing device (which is also called a processor device) and an air-supply and water-supply device, which are not illustrated in the figure, via the universal cord 16.

<Overall Configuration of Insertion Portion>

The insertion portion 12 is configured by coupling a distal end portion 12a, a bending portion 12b and a flexible portion 12c in this order from the distal end side to the proximal end side (on the side of the operation portion 14). In the insertion portion 12, a treatment tool insertion channel 19 (see FIG. 2) that guides a treatment tool to the distal end portion 12a, an operating wire 44 (see FIG. 2) used to control the derivation direction of the treatment tool led out from the distal end portion 12a, a light guide (not illustrated) that guides illumination light supplied from the light source device to the distal end portion 12a, and an air-supply and water-supply tube (not illustrated) that guides air and water supplied from the air-supply and water-supply device to the distal end portion 12a are inserted.

<Configuration of Operation Portion>

In the operation portion 14, an angle knob 18 to perform bending operation of the bending portion 12b, an elevator operation mechanism 29 (see FIG. 5) including an operating lever 20 described later used for change operation of the derivation direction of a treatment tool led out from the distal end portion 12a, an air-supply and water-supply button 21a to jet air and water, and so on, from an air-supply and water-supply nozzle (not illustrated) provided in the distal end portion 12a, and a suction button 21b to suck a body fluid such as blood from a suction port (not illustrated) provided in the distal end portion 12a, and so on, are provided.

Moreover, a treatment tool entry port 22 to introduce various treatment tools is provided on the side of the insertion portion 12 of the operation portion 14. The distal end of a treatment tool inserted in the treatment tool entry port 22 is led out from a treatment tool exit port 38a (see FIG. 2) provided in the side surface of the distal end portion 12a through the treatment tool insertion channel 19 (see FIG. 2) provided in the insertion portion 12.

<Configuration of Bending Portion>

The bending portion 12b has a configuration in which: a structure is formed by coupling unillustrated angle rings in a mutually rotatable manner; and the outer periphery of this structure is covered with a net-like body woven from metal wire and is further covered with an outer skin made of rubber. A plurality of unillustrated wires extend from the angle knob 18 of the operation portion 14 to the bending portion 12b, and the distal end portions of these wires are fixed to the distal end portions of the angle rings forming the bending portion 12b. By this means, the bending portion 12b is bent in the upper, lower, right or left direction according to the operation of the angle knob 18.

<Configuration of Flexible Portion>

The flexible portion 12c has a configuration in which: the innermost side is a spiral tube is formed by winding an elastic thin belt-shaped plate in a spiral manner, the spiral tube is then covered with a net-like body that is woven from metal wire and fitted with a metal cap at both ends thereof to form a tubular body; the outer peripheral surface of the tubular body is laminated with an outer skin formed of resin.

<Configuration of Distal End Portion>

Figure 2:
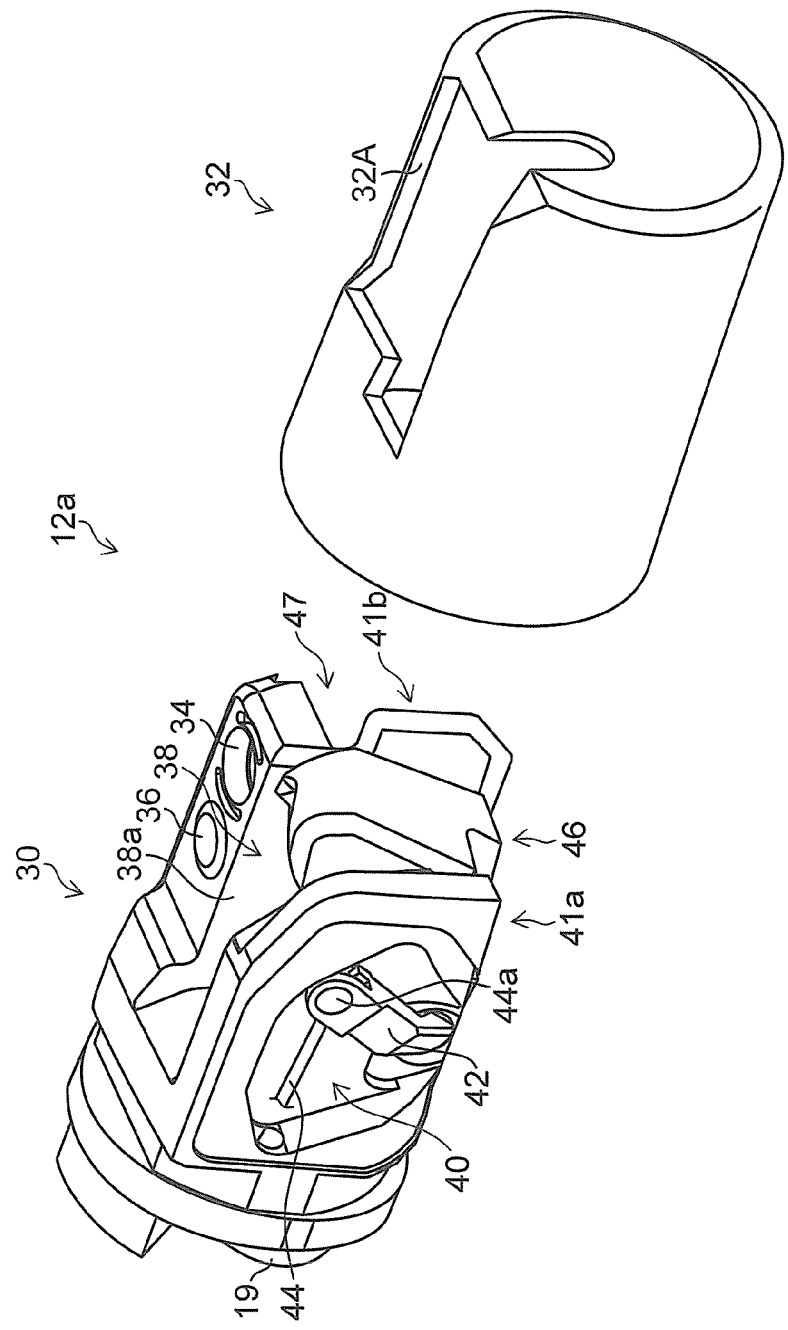
FIG. 2 is an external perspective view illustrating a structure of a distal end portion of an insertion portion.

FIG. 2 is an external perspective view illustrating the structure of the distal end portion 12a. As illustrated in FIG. 2, the distal end portion 12a has a distal end portion body 30 (body 30 of the distal end portion 12a) and a cap 32 which covers the distal end portion body 30. In the cap 32, an opening window 32A which opens the treatment tool exit port 38a that is an opening on the upper surface side of an elevator housing chamber 38 described later is formed in a state where it is attached to the distal end portion body 30. The cap 32 is made of an elastic material, for example, silicone rubber. The cap 32 includes an engagement portion which is engaged with a groove formed in the distal end portion body 30 on the proximal end side thereof and is detachably attached to the distal end portion body 30.

Figure 3:
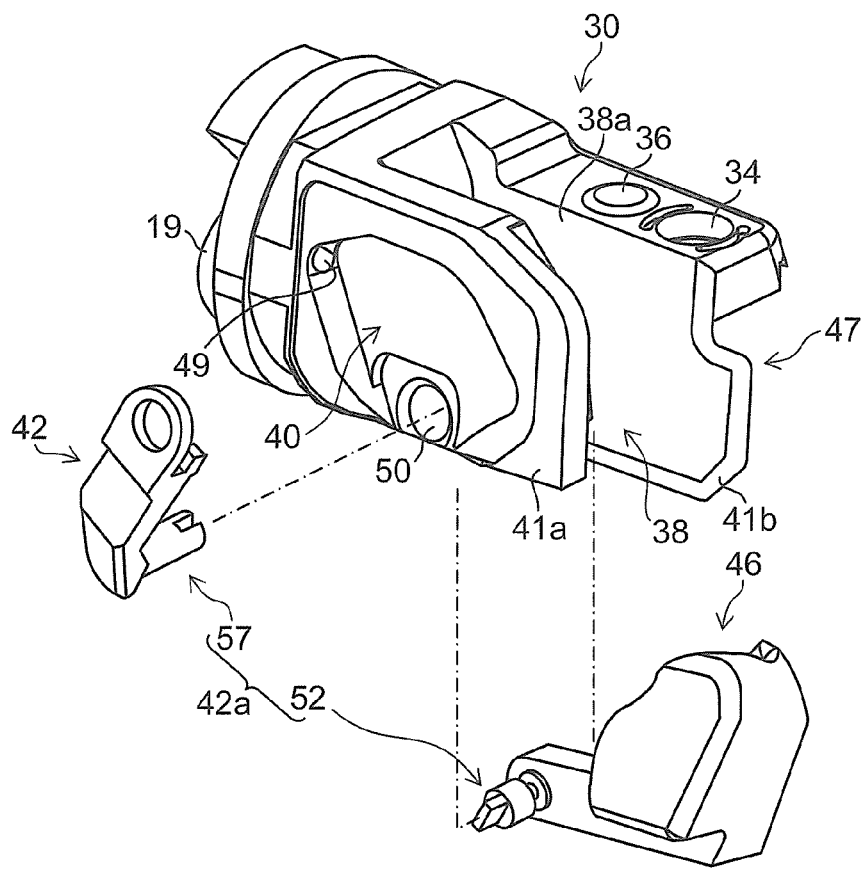
FIG. 3 is an exploded perspective view of the distal end portion.
Figure 4:
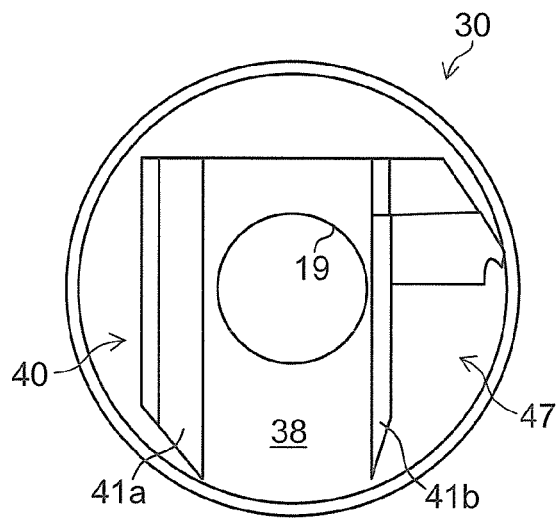
FIG. 4 is a front view of a body of the distal end portion included in the distal end portion.

FIG. 3 is an exploded perspective view of the distal end portion 12a. FIG. 4 is a front view of the distal end portion body 30. As illustrated in FIGS. 2 to 4, the distal end portion body 30 is formed of a metallic material having corrosion resistance, and includes a pair of a first partition wall 41a and a second partition wall 41b which are parts of the distal end portion body 30 and face each other. The elevator housing chamber 38 that is a slit-like space which houses an elevator 46 is formed between the first partition wall 41a and second partition wall 41b. An opening on the upper surface side of this elevator housing chamber 38 in FIG. 3 is the treatment tool exit port 38a from which the treatment tool is led out.

Moreover, the treatment tool insertion channel 19 communicates with the elevator housing chamber 38 of the distal end portion body 30. This treatment tool insertion channel 19 is connected with the treatment tool entry port 22 of the operation portion 14 through the inside of the insertion portion 12. By this means, when a treatment tool is inserted from the treatment tool entry port 22 to the treatment tool insertion channel 19, the treatment tool is guided into the elevator housing chamber 38 through the treatment tool insertion channel 19.

The elevator 46 changes the direction of the treatment tool guided from the treatment tool insertion channel 19 into the elevator housing chamber 38 and allows the treatment tool to be led out from the treatment tool exit port 38a on the side of the distal end portion body 30. This elevator 46 is swingably attached to the first partition wall 41a through a rotating shaft 42a described later, and, when the treatment tool is led out from the treatment tool exit port 38a, the elevator 46 can control the direction thereof.

The first partition wall 41a corresponds to a partition wall of the present invention. On a side of an opposite surface (opposite surface side) that is a side opposite to a side of a facing surface (facing surface side) facing the elevator housing chamber 38 of the first partition wall 41a, a concave erecting lever housing chamber 40 which houses an elevator erecting lever 42 is formed by notching a part of the opposite surface. In other words, the first partition wall 41a is provided between the elevator 46 (elevator housing chamber 38) and the elevator erecting lever 42 (erecting lever housing chamber 40).

An optical system housing chamber 47 is provided on a side of an opposite surface (opposite surface side) that is a side opposite to a side of a facing surface (facing surface side) facing the elevator housing chamber 38 of the second partition wall 41b. In other words, the second partition wall 41b is provided between the elevator 46 (elevator housing chamber 38) and the optical system housing chamber 47.

Moreover, by covering the distal end portion body 30 with an unillustrated protective plate, the airtightness of each of the erecting lever housing chamber 40 and the optical system housing chamber 47 is maintained.

An illumination window 34 and an observation window 36 are arranged in the upper part of the optical system housing chamber 47, and the air-supply and water-supply nozzle (not illustrated) is provided toward the observation window 36. The air-supply and water-supply nozzle is connected with the above-mentioned air-supply and water-supply device through the air-supply and water-supply tube (not illustrated) inserted in the insertion portion 12. Compressed air or water is jetted from the air-supply and water-supply nozzle toward the observation window 36 by operating the air-supply and water-supply button 21a of the operation portion 14, and the observation window 36 is cleaned.

An illuminating portion and an imaging portion are housed inside the optical system housing chamber 47 though their illustration is omitted. The illuminating portion includes an illumination lens installed on an inner side of the illumination window 34 and a light guide disposed such that the distal end thereof faces this illumination lens. The light guide is inserted in the insertion portion 12 of the endoscope 10, and the proximal end portion thereof is connected with the above-mentioned light source device. By this means, an illumination light from the light source device is transmitted through the light guide and emitted from the illumination window 34.

The imaging portion includes an imaging optical system arranged on an inner side of the observation window 36, and an imaging element of the CMOS (complementary metal oxide semiconductor) type or the CCD (charge coupled device) type. The imaging element is connected with the above-mentioned image processing device through a signal cable inserted in the insertion portion 12. An imaging signal of an object image, which is obtained by imaging by the imaging portion, is input in the above-mentioned image processing device through the signal cable, and the object image is displayed on a monitor of the image processing device.

A holding hole 50 that penetrates through the first partition wall 41a and communicates with the elevator housing chamber 38 is formed in the bottom surface of the concave erecting lever housing chamber 40 which houses the elevator erecting lever 42. The holding hole 50 rotatably supports the rotating shaft 42a described later which couples the elevator 46 and the elevator erecting lever 42. Here, since the elevator erecting lever 42 in the erecting lever housing chamber 40 swings around the rotating shaft 42a, the elevator housing chamber 38 is formed to have a fan-shape having the rotating shaft 42a as a center.

One end side of the elevator erecting lever 42 is coupled with the elevator 46 through the rotating shaft 42a, the other end side of the elevator erecting lever 42 is coupled with the operating wire 44. The elevator erecting lever 42 swings integrally with the elevator 46 around the rotating shaft 42a.

The operating wire 44 includes a distal-end-side coupling portion 44a (see FIGS. 6A and 6B) coupled with the elevator erecting lever 42 in the erecting lever housing chamber 40, on the distal end side thereof. Moreover, the proximal end side of the operating wire 44 is coupled with the elevator operation mechanism 29 (see FIG. 5) in the operation portion 14 through the inside of the insertion portion 12 from a wire insertion hole 49 opened to a wall surface of the erecting lever housing chamber 40.

Figure 5:
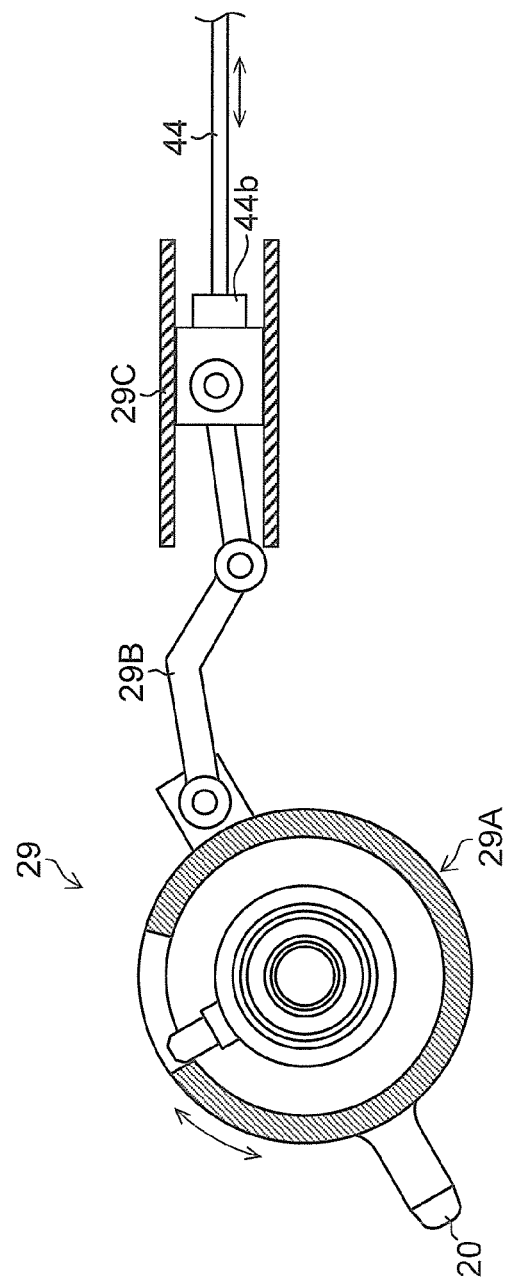
FIG. 5 is a schematic diagram illustrating one example of an elevator operation mechanism in an operation portion.

FIG. 5 is a schematic diagram illustrating one example of the elevator operation mechanism 29 in the operation portion 14. As illustrated in FIG. 5, the operating wire 44 includes a proximal-end-side coupling portion 44b coupled with the elevator operation mechanism 29, on the proximal end side thereof. The elevator operation mechanism 29 corresponds to an operating member of the present invention and includes the operating lever 20, a rotating drum 29A with which the operating lever 20 is coupled and which is rotatable within a certain angle range, a crank member 29B coupled with the rotating drum 29A, and a slider 29C coupled with the crank member 29B. The proximal-end-side coupling portion 44b is coupled with the slider 29C.

When the operating lever 20 is operated to rotate the rotating drum 29A, the elevator erecting lever 42 swings by push-pull operation of the operating wire 44 through the crank member 29B and the slider 29C, and the elevator 46 is displaced between the reclining position and the erecting position according to the swing of the elevator erecting lever 42.

Figure 6A:
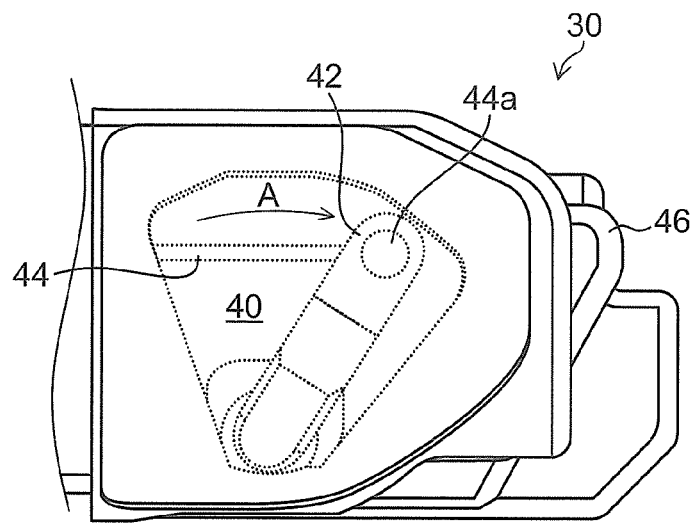
FIGS. 6A and 6B are explanatory diagrams illustrating displacement between a reclining position and erecting position of an elevator.
Figure 6B:
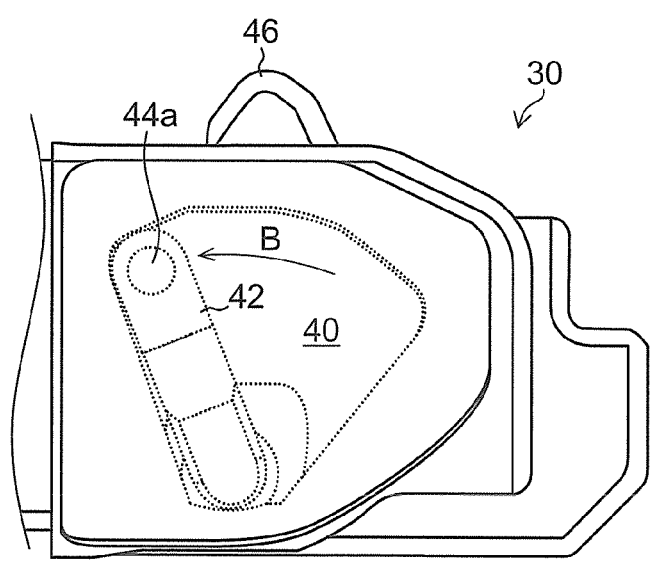

FIGS. 6A and 6B are explanatory diagrams illustrating the displacement between the reclining position and erecting position of the elevator 46. As illustrated in FIG. 6A, by push operation of the operating wire 44 when the operating lever 20 is operated to rotate the rotating drum 29A in one direction, the elevator erecting lever 42 rotates in the A direction around the rotating shaft 42a and the elevator 46 is displaced to the reclining position. Meanwhile, as illustrated in FIG. 6B, the operating wire 44 is subjected to a pull operation when the operating lever 20 is operated to rotate the rotating drum 29A in the opposite direction, the elevator erecting lever 42 rotates around the rotating shaft 42a in the B direction which is opposite to the A direction, and the elevator 46 is displaced to the erecting position. Thus, by rotating the rotating shaft 42a through the elevator erecting lever 42 by the operation of the operating lever 20, the operating wire 44 can move (erect and recline) the elevator 46.

Figure 7:
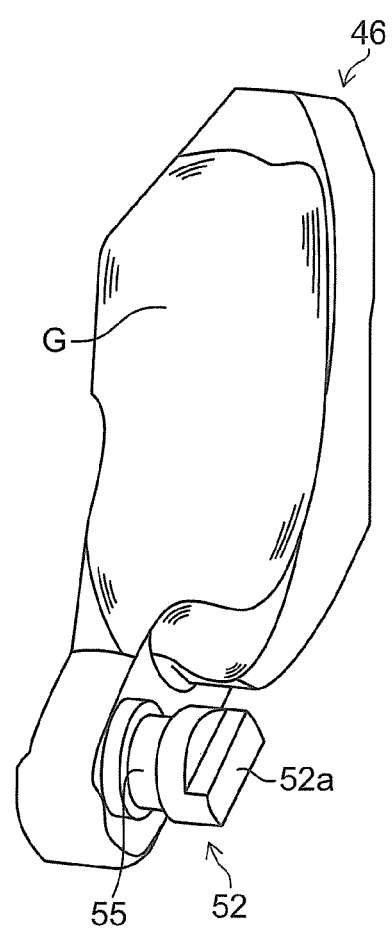
FIG. 7 is an external perspective view of an elevator housed in an elevator housing chamber.

FIG. 7 is an external perspective view of the elevator 46 housed in the elevator housing chamber 38. As illustrated in FIG. 7, in the elevator 46, a surface facing an opening portion of the treatment tool insertion channel 19 in the elevator housing chamber 38 is an arc-shaped guide surface G that guides a treatment tool, which is led out from the treatment tool insertion channel 19 into the elevator housing chamber 38, toward the treatment tool exit port 38a. Moreover, an elevator rotating shaft 52 corresponding to a second rotating shaft of the present invention is connected with the proximal end portion of the elevator 46. Here, the elevator 46 and the elevator rotating shaft 52 are connected in an airtight manner without a gap. As a method of connecting them in an airtight manner without the gap, it is possible to adopt various methods such as the integral formation of them and connection by welding of them.

One end of the elevator rotating shaft 52 is connected with the proximal end portion of the elevator 46 as mentioned above, and the other end thereof includes a convex coupling portion 52a corresponding to a second coupling portion of the present invention. The convex coupling portion 52a includes a convex portion that projects in the axis direction of the elevator rotating shaft 52. The elevator rotating shaft 52 is inserted from the side of the elevator housing chamber 38 into the holding hole 50. Moreover, a housing groove 55 which houses a ring-shaped seal member 54 (see FIG. 10) is formed in the outer peripheral surface of the elevator rotating shaft 52.

Figure 8:
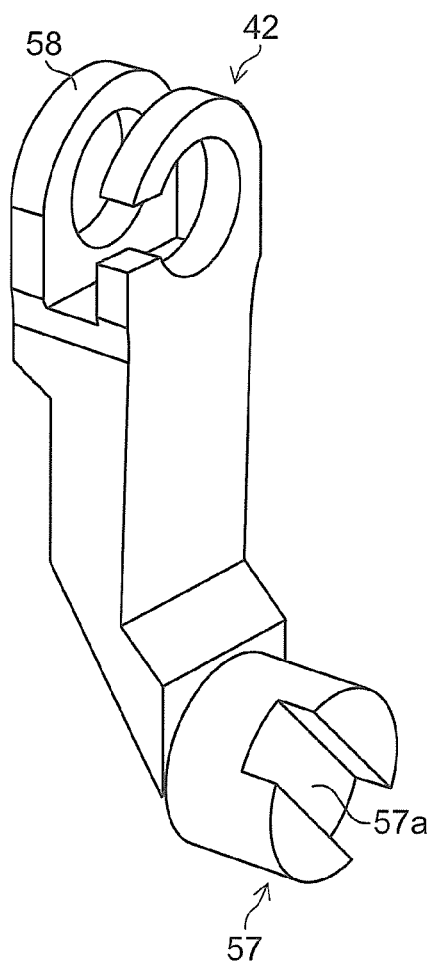
FIG. 8 is an external perspective view of an elevator erecting lever housed in an erecting lever housing chamber.

FIG. 8 is an external perspective view of the elevator erecting lever 42 housed in the erecting lever housing chamber 40. As illustrated in FIG. 8, the proximal end side of the elevator erecting lever 42 is connected to an erecting lever rotating shaft 57 corresponding to a first rotating shaft of the present invention, and a wire connection portion 58 with which the distal-end-side coupling portion 44a of the operating wire 44 led into the erecting lever housing chamber 40 is coupled, is formed on the distal end side of the elevator erecting lever 42. Here, the erecting lever rotating shaft 57 may be a discrete body which is separate from the elevator erecting lever 42.

One end of the erecting lever rotating shaft 57 is connected with the proximal end portion of the elevator erecting lever 42 as mentioned above, and the erecting lever rotating shaft 57 includes a concave coupling portion 57a corresponding to a first coupling portion of the present invention, on the other end thereof. The concave coupling portion 57a includes a concave portion that is concave in the axis direction of the erecting lever rotating shaft 57. The erecting lever rotating shaft 57 is inserted from the side of the erecting lever housing chamber 40 into the holding hole 50.

Figure 9:
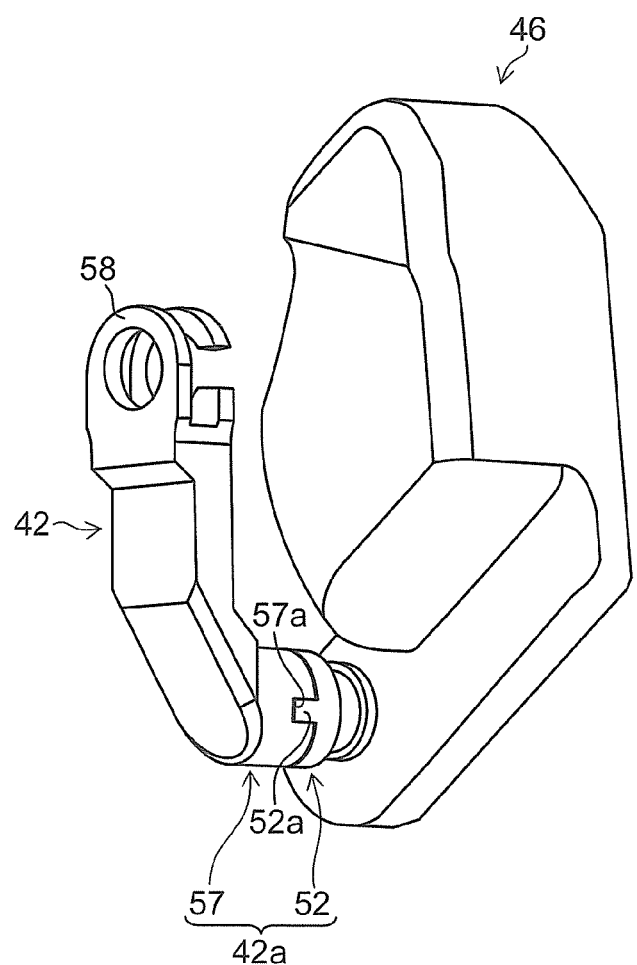
FIG. 9 is an explanatory diagram illustrating a coupling state between an elevator rotating shaft and an erecting lever rotating shaft.

FIG. 9 is an explanatory diagram illustrating a coupling state between the elevator rotating shaft 52 and the erecting lever rotating shaft 57. As illustrated in FIG. 9, in the holding hole 50 (illustration is omitted), the convex coupling portion 52a of the elevator rotating shaft 52 is coupled (fitted) with the concave coupling portion 57a of the erecting lever rotating shaft 57 in a relativity unrotatable manner. By this means, the elevator rotating shaft 52 and the erecting lever rotating shaft 57 are coupled. As a result, the elevator 46 and the elevator erecting lever 42 are coupled through the rotating shaft 42a including the elevator rotating shaft 52 and the erecting lever rotating shaft 57, and the elevator 46 and the elevator erecting lever 42 integrally swing around the rotating shaft 42a.

Figure 10:
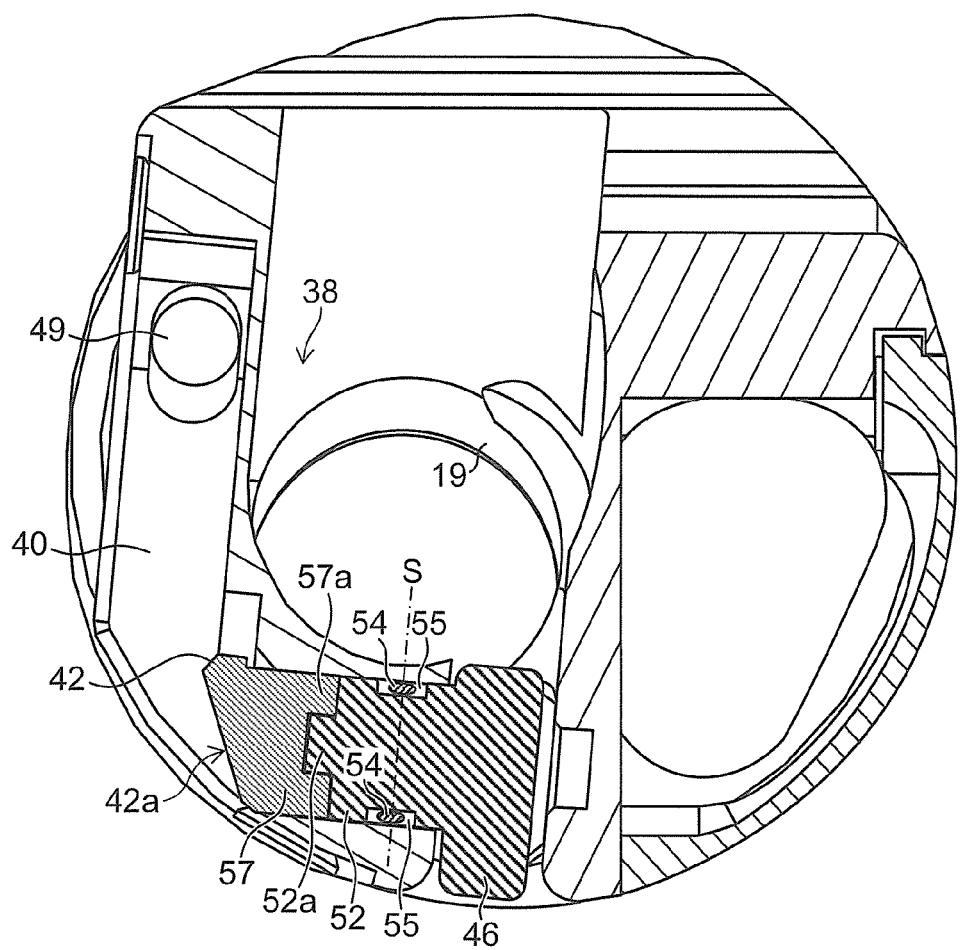
FIG. 10 is a cross-sectional view of a rotating shaft inserted in a holding hole.
Figure 11:
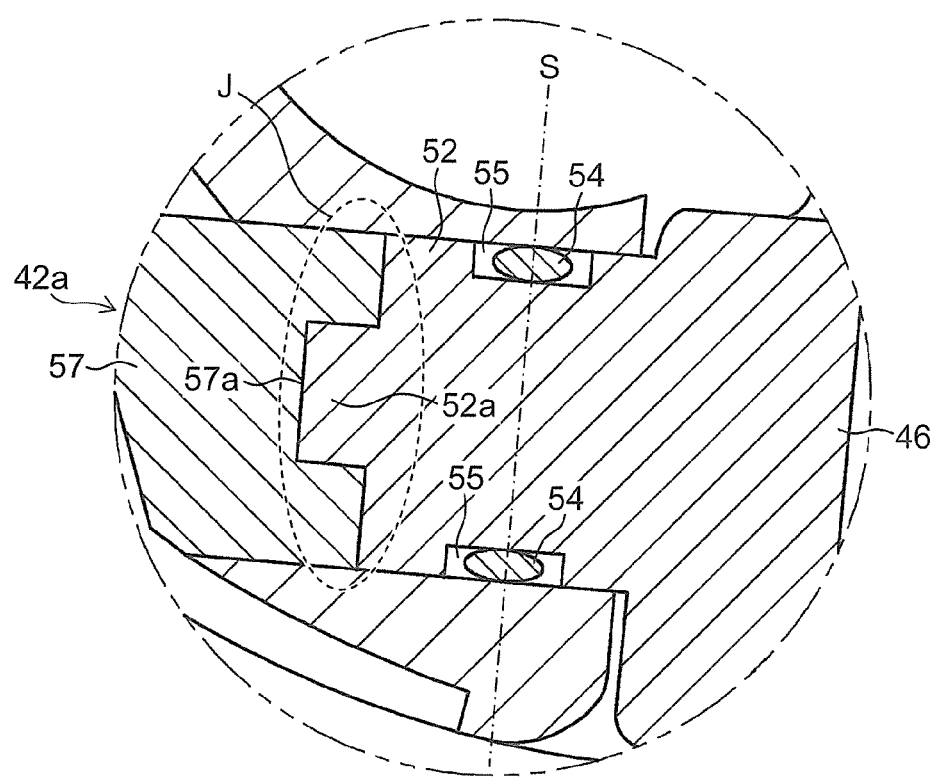
FIG. 11 is an enlarged view that enlarges a part of the cross-sectional view illustrated in FIG. 10.

FIG. 10 is a cross-sectional view of the rotating shaft 42a inserted in the holding hole 50. FIG. 11 is an enlarged view that enlarges a part of the cross-sectional view illustrated in FIG. 10. As illustrated in FIGS. 10 and 11, the ring-shaped seal member 54 which is housed in the housing groove 55 is disposed between the holding hole 50 and the rotating shaft 42a. Therefore, even if a liquid such as blood or water (which is simply abbreviated as "liquid" below) enters from the inside of the elevator housing chamber 38 into between the holding hole 50 and the rotating shaft 42a, the liquid is prevented by the seal member 54 from entering a region on the side of the elevator erecting lever 42 from the airtight surface S shown by the alternate long and short dash line in FIG. 10.

In the present embodiment, a coupling position J between the elevator rotating shaft 52 (convex coupling portion 52a) and the erecting lever rotating shaft 57 (concave coupling portion 57a) which form the rotating shaft 42a is disposed on the side of the elevator erecting lever 42 with respect to the seal member 54, that is, the airtight surface S (the rotating shaft 42a is nearer to the elevator erecting lever 42 than the seal member 54). Therefore, liquid entering from the inside of the elevator housing chamber 38 into between the holding hole 50 and the rotating shaft 42a is prevented from entering up to coupling position J.

Moreover, in the present embodiment, the side wall surface of the housing groove 55 and a part of the outer peripheral surface of the seal member 54 are engaged with each other. Even when the rotating shaft 42*a* rotates, the position of the seal member 54 in the axis direction of this rotating shaft 42*a* (which is simply abbreviated as "axis direction" below) is restricted within the housing groove 55 of the elevator rotating shaft 52. That is, the side wall surface of the housing groove 55 functions as a first engagement portion of the present invention, and the part of the outer peripheral surface of the seal member 54 functions as a second engagement portion of the present invention, and both of them function as a positioning portion of the present invention. By this means, since the position of the seal member 54 in the axis direction is situated within the holding hole 50, the seal member 54 is prevented from moving toward the side of the elevator erecting lever 42 beyond (over) the coupling position J by the rotation of the rotating shaft 42*a* and/or the slide contact with the inner wall surface of the holding hole 50. As a result, the liquid entering inside the elevator housing chamber 38 is reliably prevented from entering to reach the coupling position J.

Figure 12:
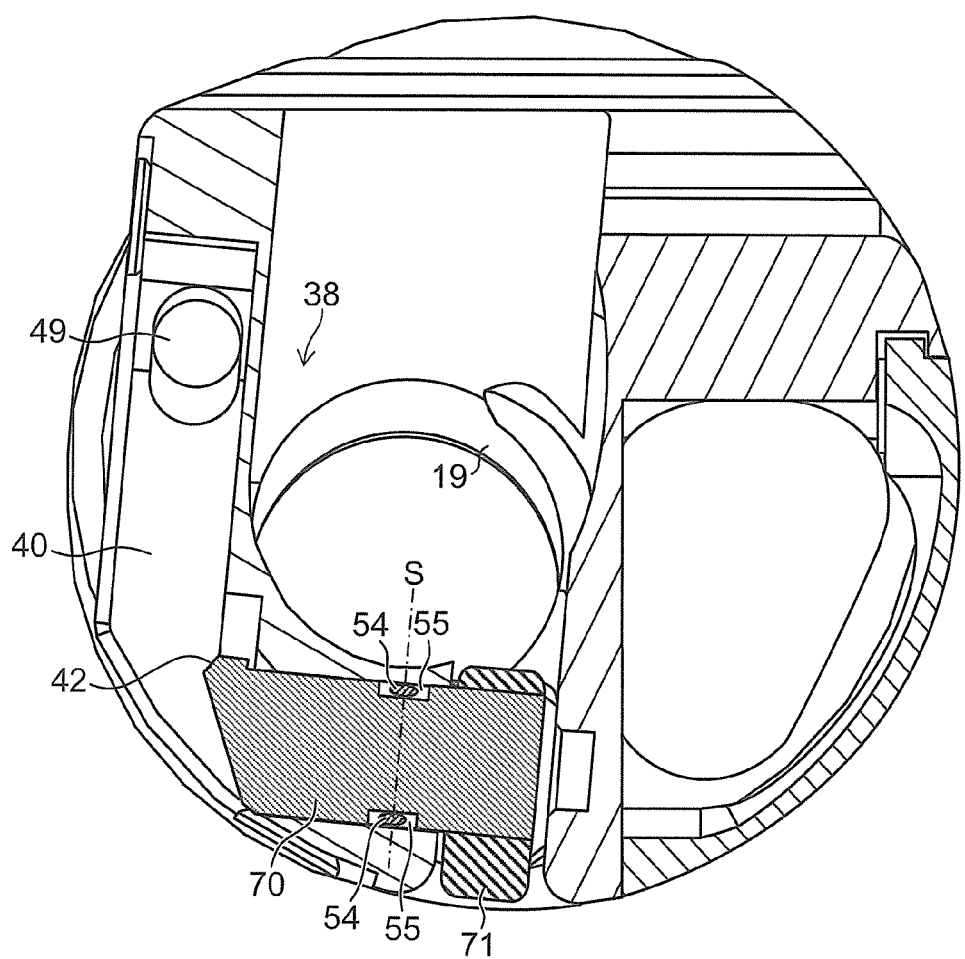
FIG. 12 is a cross-sectional view of a rotating shaft according to a comparative example.

Meanwhile, in FIG. 12 illustrating a comparative example, if a rotating shaft 70 and an elevator 71 are coupled in the elevator housing chamber 38 outside the holding hole 50, a liquid entering inside the elevator housing chamber 38 contacts with a coupling portion between the rotating shaft 70 and the elevator 71. Therefore, after the use of the endoscope 10, it is necessary to perform cleaning processing of the coupling portion between the elevator 71 and the rotating shaft 70, which is exposed in the elevator housing chamber 38. Therefore, it takes time and labor for the cleaning processing.

As compared with such a comparative example, in the present embodiment, since the coupling position J between the elevator rotating shaft 52 of the elevator 46 and the erecting lever rotating shaft 57 of the elevator erecting lever 42 is located on the side of the elevator erecting lever 42 from (with respect to) the seal member 54, a liquid does not enter up to this coupling position J, and the cleaning processing of the coupling portion between the elevator rotating shaft 52 and the erecting lever rotating shaft 57 is not necessary. Therefore, in the present embodiment, since parts in which the cleaning processing is required decrease as compared with the related art, dirt is less likely to be accumulated, and it is possible to reduce time and labor taken for the cleaning processing.

<Another Embodiment>

Figure 13:
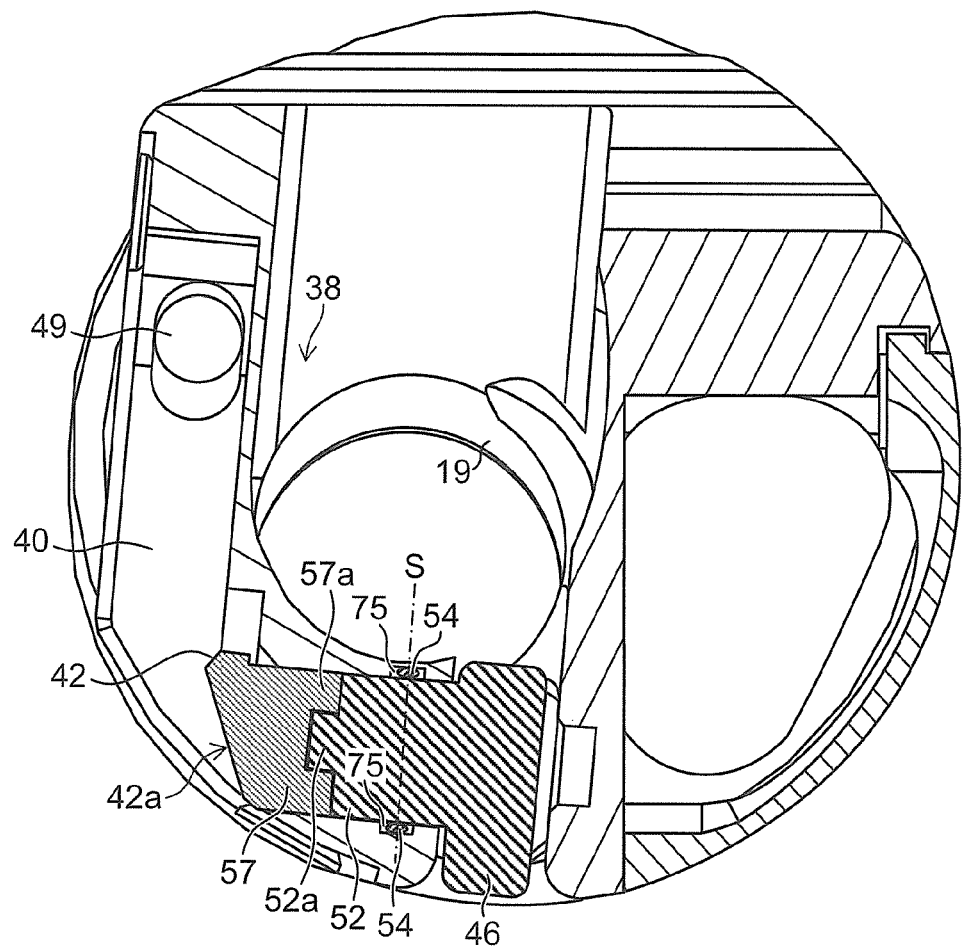
FIG. 13 is a cross-sectional view of a rotating shaft of an endoscope according to another embodiment.
Figure 14:
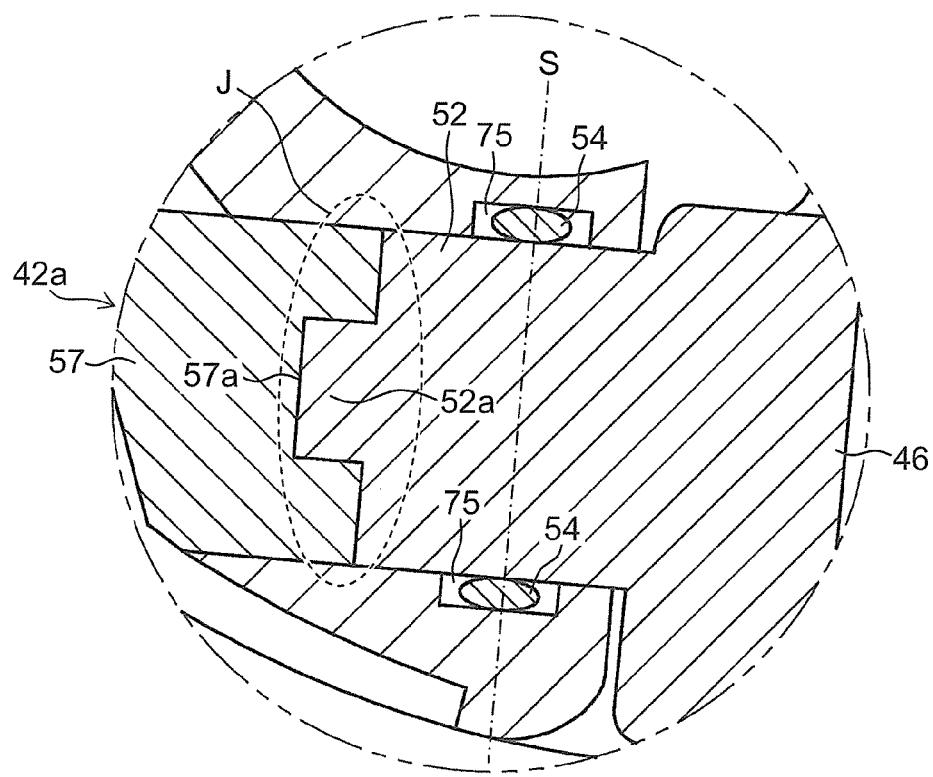
FIG. 14 is an enlarged view that enlarges a part of the cross-sectional view illustrated in FIG. 13.

FIG. 13 is a cross-sectional view of the rotating shaft 42*a* of an endoscope of another embodiment. FIG. 14 is an enlarged view that enlarges a part of the cross-sectional view illustrated in FIG. 13. The housing groove 55 which houses the seal member 54 is formed in the outer peripheral surface of the elevator rotating shaft 52 in the above-mentioned embodiment. On the other hand, as illustrated in FIGS. 13 and 14, a housing groove 75 which houses the seal member 54 may be formed in the inner wall surface of the holding hole 50 of a second partition wall facing the outer peripheral surface of the elevator rotating shaft 52. In this case, the side wall surface of the housing groove 75 functions as a first engagement portion of the present invention, a part of the outer peripheral surface of the seal member 54 functions as a second engagement portion of the present invention, and both of them function as a positioning portion of the present invention. Therefore, the position of the seal member 54 in the axis direction is situated within the housing groove 75.

As a result, an effect similar to the above-mentioned embodiment can be obtained.

<Others>

The position of the seal member 54 in the axis direction is determined from the housing groove 55 or the housing groove 75 in each above-mentioned embodiment. However, as long as the seal member 54 can be prevented from moving toward the side of the erecting lever housing chamber 40 from the coupling position J, a positioning method of the position of the seal member 54 in the axis direction is not especially limited.

In each above-mentioned embodiment, the elevator rotating shaft 52 and the erecting lever rotating shaft 57 are coupled with each other in a relatively unrotatable manner by coupling the convex coupling portion 52*a* and the concave coupling portion 57*a*. However, the shape of the coupling portion between the elevator rotating shaft 52 and the erecting lever rotating shaft 57 is not especially limited. It is possible to adopt various shapes that can couple them in a relatively unrotatable manner, for example, such as a polygonal shaft (square shaft) shape or the like. Moreover, a concave coupling portion (concave portion) may be formed in the elevator rotating shaft 52 which is one of the elevator rotating shaft 52 and the erecting lever rotating shaft 57, and a convex coupling portion (convex portion) may be formed in the erecting lever rotating shaft 57 which is the other of them.

The side wall surface of the housing groove 55 or the housing groove 75 is engaged with a part of the outer peripheral surface of the seal member 54 in each above-mentioned embodiment. However, an engagement portion (second engagement portion of the present invention) may be formed in the seal member 54 to have a various shape which can be engaged with the side wall surface of the housing groove 55 or the like. For example, a part of the outer peripheral surface of the seal member 54 facing the side wall surface of the housing groove 55 or the like may be formed in a plane shape.

Explanation has been given using the elevator operation mechanism 29 which includes the operating lever 20 as an example of an operating member to displace the elevator 46 between the reclining position and the erecting position in each above-mentioned embodiment, but known various operating members may be used.

Explanation has been given using a side-view endoscope as an example in each above-mentioned embodiment, but the present invention is applicable to various endoscopes such as an ultrasonic endoscope and a direct-view endoscope which include an elevator that adjusts the derivation direction of a treatment tool in the distal end portion of an insertion portion.

What is claimed is:

1. An endoscope comprising:
    an insertion portion which includes a distal end and a proximal end;
    an operation portion which is provided on a proximal end side of the insertion portion and includes an operating member;
    a distal end portion body which is provided on a distal end side of the insertion portion;
    a rotating shaft which is rotatably supported in the distal end portion body;
    an elevator which is coupled with one end of the rotating shaft;
    an elevator erecting lever which is coupled with the other end of the rotating shaft;

an operating wire which includes a proximal-end-side coupling portion coupled with the operating member and a distal-end-side coupling portion coupled with the elevator erecting lever, the operating wire configured to rotate the rotating shaft through the elevator erecting lever by operation of the operating member to erect the elevator;

a partition wall which includes a holding hole to support the rotating shaft, is a part of the distal end portion body and is provided between the elevator and the elevator erecting lever; and a seal member which is disposed between the holding hole and the rotating shaft, wherein:

the rotating shaft includes a first rotating shaft and a second rotating shaft;

the first rotating shaft has one end connected with the elevator erecting lever and another end provided with a first coupling portion;

the second rotating shaft has one end that is integrally formed with the elevator or connected with the elevator by welding of the one end and the elevator, and another end provided with a second coupling portion which is coupled with the first coupling portion in a relativity unrotatable manner; and a coupling position in which the first coupling portion and the second coupling portion are coupled with each other is disposed on a side of the elevator erecting lever with respect to the seal member.

2. The endoscope according to claim 1, wherein:

any one of the first coupling portion and the second coupling portion has a convex portion that projects in an axis direction of the rotating shaft;

another one of the first coupling portion and the second coupling portion includes a concave portion that is concave in the axis direction of the rotating shaft; and the first rotating shaft and the second rotating shaft are coupled in a relatively unrotatable manner by fitting the convex portion and the concave portion to each other.

3. The endoscope according to claim 1, further comprising a positioning portion configured to position the seal member in an axis direction of the rotating shaft, wherein the positioning portion includes a first engagement portion provided in the second rotating shaft and a second engagement portion provided in the seal member, and positions the seal member in the axis direction by engaging the first engagement portion and the second engagement portion with each other.

4. The endoscope according to claim 1, further comprising a positioning portion configured to position the seal member in an axis direction of the rotating shaft, wherein the positioning portion includes a first engagement portion provided in an inner wall surface of the holding hole of the partition wall and a second engagement portion provided in the seal member, and positions the seal member in the axis direction by engaging the first engagement portion and the second engagement portion with each other.

5. The endoscope according to claim 1, wherein the second rotating shaft has one end connected with the elevator in an airtight manner without a gap.

6. The endoscope according to claim 1, wherein an axis passes through rotation centers of the first rotating shaft and the second rotating shaft.

7. The endoscope according to claim 2, wherein the coupling position at which the convex portion and the concave portion are fitted to each other is positioned in the holding hole.

* * * * *